United States Patent [19]

Barner et al.

[11] 4,153,614
[45] May 8, 1979

[54] SYNTHESIS OF (S)-(+)-6-HYDROXY-2,5,7,8-TETRAMETHYL-CHROMAN-2-METHANOL AND INTERMEDIATES THEREIN

[75] Inventors: Richard Barner, Witterswil; Max Schmid, Brugg, both of Switzerland

[73] Assignee: Hoffmann-La Roche Inc., Nutley, N.J.

[21] Appl. No.: 905,361

[22] Filed: May 12, 1978

[51] Int. Cl.$^2$ .................................. C07D 317/10
[52] U.S. Cl. .......................... 260/340.9 R; 260/345.2; 260/396 R; 260/606.5 F; 560/186; 568/763; 568/649
[58] Field of Search ................ 260/340.9 R, 333

[56] References Cited

U.S. PATENT DOCUMENTS

| 2,815,351 | 12/1957 | Stansbury | 260/340.9 R |
| 3,654,311 | 4/1972 | Isard et al. | 260/340.9 R |
| 4,113,740 | 9/1978 | Cohen et al. | 260/340.9 R |

FOREIGN PATENT DOCUMENTS 768685  2/1957  United Kingdom ............ 260/340.9 R

*Primary Examiner*—Ethel G. Love
*Attorney, Agent, or Firm*—Jon S. Saxe; Bernard S. Leon; William H. Epstein

[57] ABSTRACT

A process if disclosed for producing (S)-(+)-6-hydroxy-2,4,7,8-tetramethylchroman-2-methanol from either alkyl(R)-2-benzyloxy-3-hydroxy-2-methyl-propionate or (S)-2,2,4-trimethyl-1,3-dioxolan-4-ethanol including intermediates in this synthesis.

1 Claim, No Drawings

SYNTHESIS OF (S)-(+)-6-HYDROXY-2,5,7,8-TETRAMETHYL-CHROMAN-2-METHANOL AND INTERMEDIATES THEREIN

BACKGROUND OF THE INVENTION

According to prior art processes, natural optically active Vitamin E which is the 2R,4′R,8′R isomer of α-tocopherol, is manufactured from a known aldehyde of the formula:

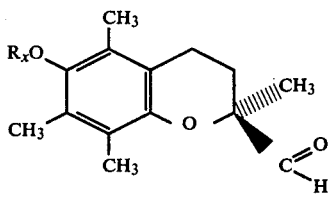

VI wherein $R_x$ is lower alkyl, lower alkanoyl or benzyl.

The prior art process for producing this aldehyde, however, presents many problems. For example, an acid firstly obtained in the manufacture of the above aldehyde is always produced in racemic form and can be separated into its optical antipodes only in an extremely complicated manner. Further, the undesired antipode of the acid cannot be racemized and restored into the process which accordingly leads to considerable material loss.

We have invented an improved process for producing the aldehyde of formula I via optically active intermediates which avoids the difficulties of the prior art.

SUMMARY OF THE INVENTION

According to the present invention, a compound of the formula:

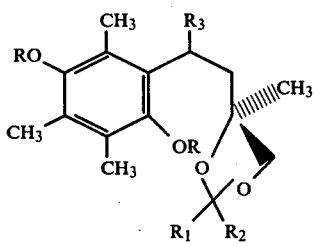

I is oxidized with a cerium(IV) salt or complex to form quinones of the formulas:

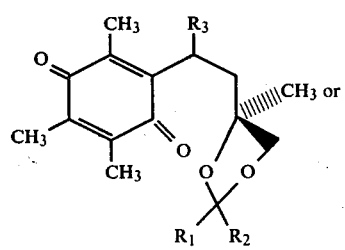

II

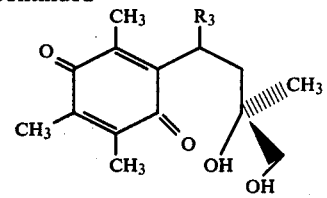

III wherein R is lower alkyl; $R_1$ and $R_2$ each are lower alkyl or $R_1$ is phenyl and $R_2$ is hydrogen; and $R_3$ is hydrogen or hydroxy.

Compounds II and/or III can be treated with an acid to obtain a compound of the formula:

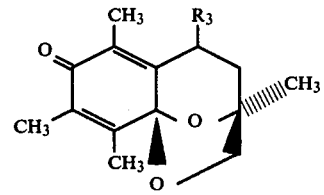

IV wherein $R_3$ is as above.

Compound IV in turn can be converted by reductive aromatization into a chromane derivative of the formula:

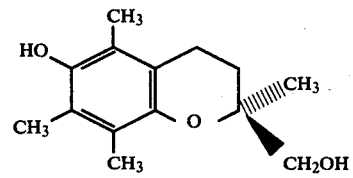

V with cleavage of hydroxy where $R_3$ is other than hydrogen.

DETAILED DESCRIPTION OF THE INVENTION

As used herein, the term "lower alkyl" refers to straight or branched chain alkyl groups having from 1 to 4 carbon atoms (e.g. methyl, ethyl, propyl and isopropyl).

"Lower alkoxy" denotes straight or branched chain alkoxy groups of 1 to 6 carbon atoms (e.g. methoxy, ethoxy and isopropoxy).

"Lower alkanoyl" signifies moieties derived from alkanecarboxylic acid moieties having 1 to 6 carbon atoms (e.g. formyl, acetyl, propionyl, etc.).

"Halogen" includes all four halogens, i.e. fluorine, chlorine, bromine and iodine.

"Lower alkylene" refers to straight and branched chain alkylene groups having from 1 to 6 carbon atoms (e.g. methylene, ethylene and propylene).

"Aryl" designates mononuclear aromatic hydrocarbon groups such as phenyl, tolyl, etc. which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, azulyl, etc., which can be unsubstituted or substituted with one or more of the aforementioned groups. The preferred aryl groups are the substituted and unsubstituted mononuclear aryl groups, particularly phenyl.

Of the inorganic acid anions there are preferred chlorine, bromine and iodine ions or the hydrosulfate ion and of the organic acid anions there is preferred the tosyloxy ion.

"Alkali metal" includes all alkali metals such as lithium, sodium, potassium, rubidium and cesium.

In the pictorial representation of the compounds given throughout this application, a ( ) tapered line indicates a substituent which is pointed out of the plane of the paper towards the reader and the (---) broken line indicates a substituent which is pointed into the plane of the paper away from the reader.

In accordance with a preferred process of the present invention, a compound of the formula:

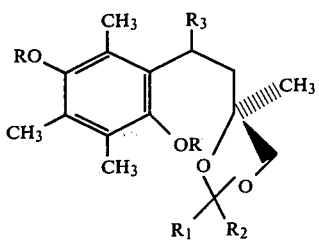

I is oxidized with a cerium(IV) salt or complex to form quinones of the formulas:

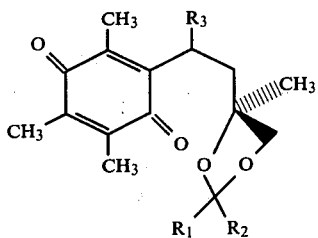

II and

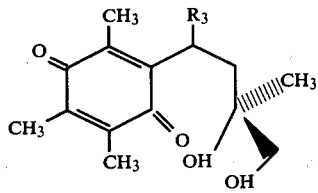

III wherein R is lower alkyl, $R_1$ and $R_2$ each are lower alkyl or $R_1$ is phenyl and $R_2$ is hydrogen; and $R_3$ is hydrogen or hydroxy.

In carrying out this oxidation, any conventional cerium-(IV) salt or complex can be utilized. Suitable cerium compounds are, for example, cerium sulfate or cerium ammonium nitrate. The oxidation is conveniently carried out in an inert organic solvent which is miscible with water (e.g. acetonitrile, tetrahydrofuran and the like) at a temperature of about $-10°$ C. to about $40°$ C. Preferably, the oxidation occurs at a temperature between about $10°$ C. and about $30°$ C.

Compounds II, III or mixtures thereof (which mixtures are separable by chromatography, e.g. on silica gel) can be treated with an acid to obtain a compound of the formula:

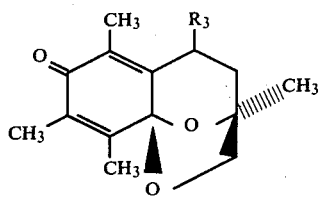

IV wherein $R_3$ is as above.

Suitable acids include mineral acids (e.g. dilute sulfuric acid, dilute hydrochloric acid, dilute phosphoric acid and the like) as well as organic acids (e.g. formic acid, acetic acid, trifluoroacetic acid, p-toluenesulfonic acid and the like). The reaction is also conveniently effected, especially in the case of the use of a mineral acid, in an inert organic solvent which is miscible with water such as lower alcohols (e.g. methanol, ethanol, propanol, etc.), ether (e.g. dioxan, tetrahydrofuran etc., diethyleneglycol and dimethyl ether), acetonitrile, dimethylformamide and the like, at a temperature of about room temperature to about $100°$ C. Preferably, the reaction proceeds from about room temperature to about $70°$ C.

Where the previously described oxidation of compound I is carried out in an acid medium, compound I can thereby be converted directly into compound IV.

Compound IV can then be converted by reductive aromatization into a chromane derivative of the formula:

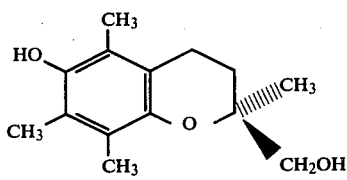

V with cleavage of the hydroxy group where $R_3$ is other than hydrogen.

Where $R_3$ in the compound of formula IV is hydrogen, the reductive aromatization is conveniently effected by hydrogen in the presence of a catalyst (e.g. palladium or platinum) with or without a carrier, as well as by complex hydrides (e.g. lithium aluminum hydride, diisobutylaluminium hydride, NaAlH$_2$(OCH$_2$CH$_2$OCH$_3$)$_2$ and the like) in a suitable organic solvent or also by zinc in acetic acid and the like.

Where $R_3$ in the compound of formula IV signifies hydroxy, the reductive aromatization is conveniently effected with previous cleavage of the hydroxy group. This clevage can be carried out by treatment with hydrogen in the presence of a catalyst such as palladium with or without a carrier material, as well as in the presence of a catalytic amount of a mineral acid (e.g. perchloric acid, hydrochloric acid and the like) which does not poison the catalyst, or in the presence of a strong organic acid (e.g. p-toluenesulfonic acid and the like). Any conventional hydrogenation catalyst can be utilized in carrying out this reaction.

Alternatively, the conversion of compound IV, wherein $R_3$ signifies the hydroxy group, into compound V can also be carried out in a "one-pot process". That is, the reaction can proceed without any isolation of the formed intermediate products of the formulae IIA, III or IV, wherein R represents hydrogen. The compound of the formula:

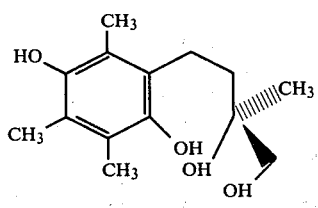

IIIa which is obtained after the cleavage of the hydroxy group from the compound of formula IV spontaneously converts in the presence of oxygen into a compound III, wherein R₃ signifies hydrogen. The further conversion of compound III into compound V is then effected as previously stated. If it is desired to produce the compound of formula IIIa from the compound of formula IV, the reduction is carried out in an oxygen-free atmosphere, i.e. under nitrogen.

The compound of the formula V is known and can be converted in a known manner into the corresponding (likewise known) aldehyde of the formula:

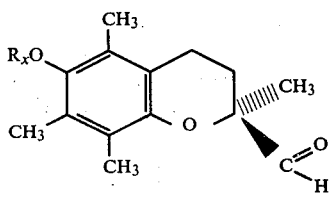

VI wherein $R_x$ is lower alkyl, lower alkanoyl of benzyl. Aldehyde VI can then be converted into natural (2R, 4'R,8'R)-α-tocopherol, likewise in a known manner. For example, aldehyde VI can be reacted with a compound of the formula:

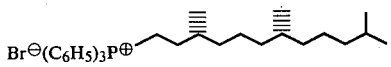

via a Wittig reaction and subsequent catalytic hydrogenation.

In accordance with the present invention, it is hereby possible to manufacture the optically active aldehyde VI or compound V which are required for the manufacture of natural (2R,4'R,8'R)-α-tocopherol in a synthetic manner from optically active starting material with retention of the absolute configuration at the tertiary carbon atom.

The compounds of the above formula I, used as the starting material in the inventive process, can be manufactured, depending on the significance of the substituents R₃, according to following Scheme I or II.

Compound I, wherein R₃ is hydrogen, can be prepared in accordance with Scheme I.

Scheme I
R₃ = hydrogen

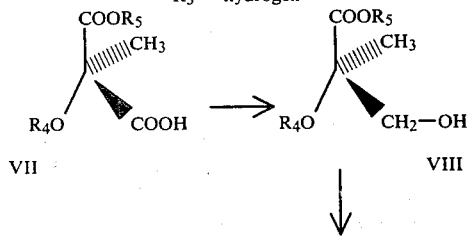

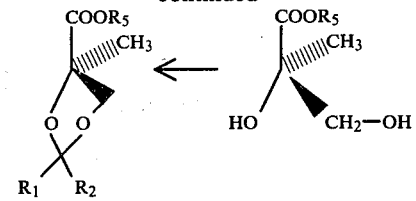

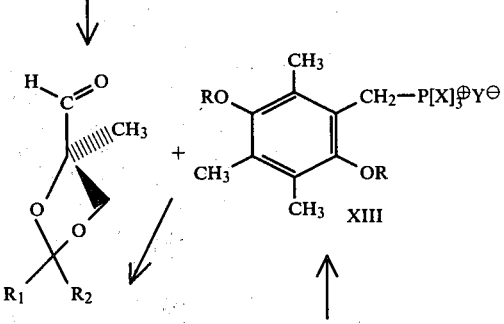

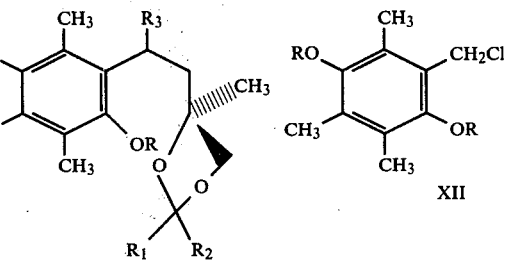

In Scheme I, the substituents R, R₁ and R₂ are as above; R₃ is hydrogen; R₄ is benzyl; R₅ is lower alkyl; X is aryl and Y is an anion of an organic or inorganic acid.

Compound VII, used as the starting material in Scheme I, is known.

The conversion of compound VII into compound VIII can be effected in a known manner. For example, compound VII can be reacted with thionyl chloride in an inert organic solvent (e.g. dimethylformamide or an ether) at a temperature of about 0° C. to about 40° C. followed by reduction of the obtained acid chloride (e.g. with sodium borohydride in dimethylformamide).

The conversion of compound VIII into compound IX, i.e. the cleavage of benzyl R₄, can likewise be effected in a known manner. Conveniently, this cleavage is carried out by catalytic hydrogenation. Any organic solvent which is inert under the reaction conditions can be conveniently utilized. Suitable solvents include ethyl acetate, methanol, ethanol and the like. A typical catalyst is palladium/carbon catalyst.

The conversion of compound IX into compound X can be carried out in a known manner. For example, compound IX can be reacted with a 2,2-di-lower alkoxypropane (e.g. 2,2-dimethoxypropane) or a di-lower alkyl-ketone (e.g. acetone) or also with benzaldehyde, in the presence of a catalytic amount of an acid, (e.g. p-toluenesulfonic acid, phosphorus oxychloride, sulfuric acid and the like), at a temperature of about 0° C. to about 50° C.

The conversion of compound X into compound XI can be effected directly and in a known manner. Conveniently, the conversion is effected with diisobutylaluminium hydride in an inert organic solvent such as an ether or hydrocarbon (e.g. hexane and the like), at a temperature of about −60° C. to about −80° C.

The conversion of compound XII into compound XIII can be carried out in a known manner. For example, the conversion can be effectuated by reacting compound XII with triphenylphosphine in toluene or benzene.

The reaction of compound XI with compound XIII to give a compound of formula I is effected in a known manner. Illustratively, a Wittig procedure can be utilized. In so doing, the Wittig components are reacted with one another in the presence of a strong base, (e.g. in the presence of an alkali metal alcoholate, such as sodium methylate, or in the presence of an optionally alkyl-substituted alkylene oxide, especially in the presence of ethylene oxide or 1,2-butylene oxide) optionally in a solvent, (e.g. in a chlorinated hydrocarbon, such as methylene chloride, or also in dimethylformamide) in a temperature range between room temperature and the boiling point of the reaction mixture.

Compound I, wherein $R_3$ is hydroxy, can be manufactured in accordance with following Scheme II.

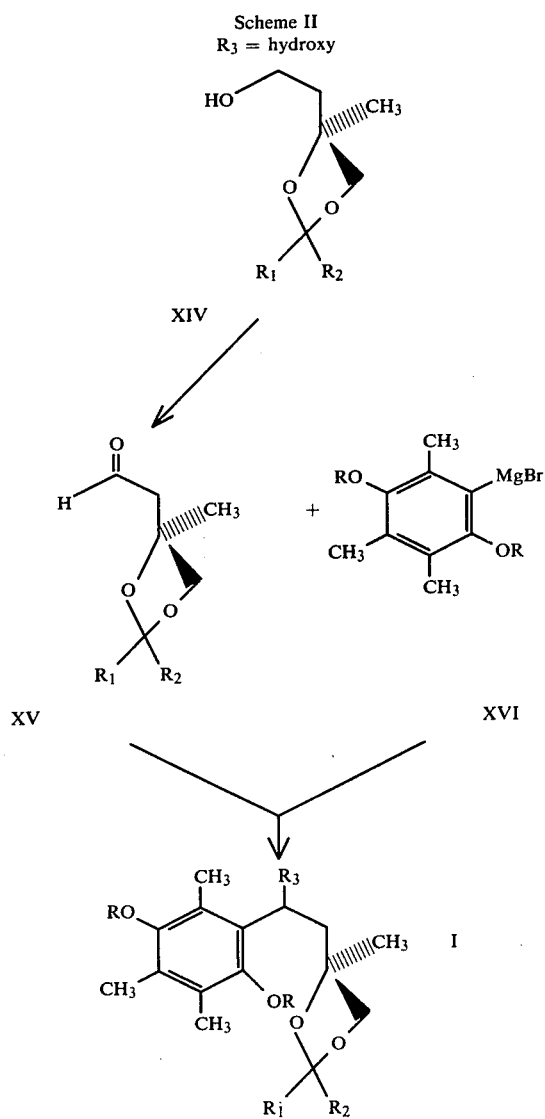

In Scheme II, the substituents R, $R_1$ and $R_2$ are as above and $R_3$ is hydroxy.

Compounds XIV and XVI, used as the starting material in the Scheme II, are known or are analogs of known compounds. In the latter situation, the compounds of formulas XIV and XVI can be obtained readily in an analogous manner to the manufacture of the known compounds. On the contrary, compound XV is novel and constitutes an object of the present invention.

The reaction of compound XIV to yield aldehyde XV can be effected in a known manner. Conveniently, the reaction is carried out by an oxidation agent chromium trioxide in pyridine or pyridine chlorochromate and the like) in an inert organic solvent (e.g. chloroform, methylene chloride, pyridine, etc.) and at a temperature of about 0° C. to about 40° C.

The reaction of compound XV with compound XVI is likewise effected in a known manner. Conveniently, the reaction proceeds in an organic solvent which is inert under the reaction conditions, such as an ether (e.g. diethyl ether, tetrahydrofuran and the like) and at a temperature between about 0° C. and the reflux temperature of the reaction mixture.

The following non-limiting Examples illustrate the invention. Unless otherwise indicated, temperature is expressed in degrees Celsius and the ether is diethyl ether.

EXAMPLE 1

Manufacture of ethyl (R)-2-benzyloxy-3-hydroxy-2-methyl-propionate

To a solution of 34.2 g of ethyl (R)-2-benzyloxy-2-methyl-monomalonate in 60 ml of methylene chloride were added dropwise while stirring at 5°, 11 g of dry dimethylformamide, followed by 11 ml of freshly distilled thionyl chloride. The reaction mixture was thereupon left to stand at room temperature for 20 hours with exclusion of moisture. The volatile components were removed by distillation at 80°, firstly at 12 mmHg and then at 0.1 mmHg. The residual liquid was finally distilled at 120° and 0.08 mmHg, there being obtained 33.4 g of a colorless oil. To this oil there was added dropwise at −30° and while stirring for 45 minutes a solution of 3.05 g of sodium borohydride in 50 ml of dry dimethylformamide. The resulting mixture was stirred at room temperature for a further 3 hours. 5 ml of 1-N sodium bicarbonate solution were added dropwise thereto while stirring, followed by 10 g of solid sodium bicarbonate, whereupon the stirring was continued during a further 1 hour. The reaction mixture then was filtered. The residue was washed with 90% dimethylformamide and the greater part of the solvent was removed from the filtrate. The residue was taken up in 250 ml of ether and washed twice with 100 ml of distilled water each time and then with 50 ml of saturated brine. After removal of the solvent, impurities were distilled off at 120°/0.1 mmHg and there were obtained 22 g of ethyl (R)-2-benzyloxy-3-hydroxy-2-methyl-propionate, $[\alpha]_D = +2.57°$ (undiluted).

EXAMPLE 2

Manufacture of ethyl (R)-2,3-dihydroxy-2-methyl-propionate 22 g of ethyl (R)-2-benzyloxy-3-hydroxy-2-methyl-propionate (manufactured in accordance with Example 1) in 150 ml of ethyl acetate were hydrogenated with hydrogen gas in the presence of 11 g of 5% by weight palladium/carbon catalyst up to the cessation of the hydrogen uptake. The catalyst was filtered off, washed with ethyl acetate (2×50 ml), the filtrate was concentrated in the vacuum and the residual oil was distilled at 56–57°/0.1 mmHg. There were obtained 12.7 g of ethyl (R)-2,3-dihydroxy-2-methyl-propionate in the form of a colorless viscous liquid. $[\alpha]_D = +0.339°$ (undiluted); $= +11.6°$ (c=2.12 in chloroform).

EXAMPLE 3

Manufacture of ethyl (R)-2,2,4-trimethyl-1,3-dioxolan-4-carboxylate 500 mg of p-toluenesulfonic acid were added to 10.7 g of ethyl (R)-2,3-dihydroxy-2-methylpropionate, dissolved in 35 ml of dry, freshly distilled 2,2-dimethoxypropane, and the mixture was stirred at room temperature overnight. The excess dimethoxypropane was removed at 45°/12 mmHg and the residue was vigorously stirred for 30 minutes with 5 ml of 1-N sodium bicarbonate. Then, 150 ml of ether were added thereto and the aqueous phase was separated. The ether solution was washed with saturated brine and then dried over sodium sulfate. After evaporation of the solvent, the product was distilled and there were obtained 11.2 g of ethyl (R)-2,2,4-trimethyl-1,3-dioxolan-4-carboxylate in the form of a colorless liquid; boiling point 81°/15 mmHg.

EXAMPLE 4

Manufacture of (R)-4-formyl-2,2,4-trimethyl-1,3-dioxolan

To a solution of 5 g of ethyl (R)-2,2,4-trimethyl-1,3-dioxolan-4-carboxylate in 30 ml of anhydrous ether, cooled down to −78°, were added dropwise while stirring for about 30 minutes, 4.55 g of diisobutylaluminium hydride in 25 ml of anhydrous ether. The temperature was held at −78° during the entire addition. The stirring was continued at −70° for a further 5 hours in order to complete the reaction. Excess reagent was then decomposed by cautious addition of a mixture of 2 ml of methanol and 2 ml of water, the cooling bath was removed and the reaction mixture was slowly brought to room temperature. While vigorously stirring under ice-cooling, 5 ml of 1-M sodium bicarbonate were added thereto. The addition of a total of 3 g of solid sodium bicarbonate in small portions led to the precipitation of aluminium hydroxide. After further vigorous stirring at 0° for 30 minutes, the precipitate was filtered off and washed three times with 30 ml of ether. The combined ether phases were dried over magnesium sulfate and the solvent was distilled off under normal pressure at about 65° bath temperature. The residue was distilled at about 80° bath temperature and 12 mmHg and there were thus obtained 3.2 g of (R)-4-formyl-2,2,4-trimethyl-1,3-dioxolan.

A once more distilled and worked-up sample was characterized as the semi-carbazone and the sample had a melting point of 201°–203°.

EXAMPLE 5

Manufacture of (S)-4-(2,5-dimethoxy-3,4,6-trimethyl-phenethyl)-2,2,4-trimethyl-1,3-dioxolan 1.84 g of (R)-4-formyl-2,2,4-trimethyl-1,3-dioxolan, 11.0 g of 2,5-dimethoxy-3,4,6-trimethylbenzyl-triphenylphosphonium chloride and 3.3 g of finely ground anhydrous potassium carbonate were heated at reflux for 30 hours in 25 ml of dry acetonitrile (dried over phosphorus pentoxide and distilled over potassium carbonate) in the presence of 55 mg of 18-crown-6 (1,4,7,10,13,16-Hexa-oxo-cyclooctadecane) the suspension being vigorously stirred. Thereupon, the brown suspension was chromatographed on 400 g of silica gel with toluene-methyl acetate-pentane (20:3:3 parts by volume) as the elution agent. After bulb-tube distillation at 170° (bath temperature)/0.2 mmHg, there were obtained 2.57 g of (S)-4-(2,5-dimethoxy-3,4,6-trimethyl-styryl)-2,2,4-trimethyl-1,3-dioxolan as a colorless viscous oil; $[\alpha]_D^{20} = +17.9°$ (c=2.1 in chloroform).

A solution of 2.51 g of (S)-2-(2,5-dimethoxy-3,5,6-trimethyl-styryl)-2,2,4-trimethyl-1,3-dioxolan in 50 ml of ethyl acetate were shaken together with 0.5 g of platinum/carbon catalyst (10% by weight) in a hydrogen atmosphere up to the cessation of the hydrogen uptake (ca 220 ml; ca 1 hour). Thereupon, the catalyst was filtered off and washed with ethyl acetate. After evaporation of the solvent, followed by a bulb-tube distillation of the residue at 180° (bath temperature)/0.6 mmHg, there were obtained 2.4 g of (S)-4(2,5-dimethoxy-3,4,6-trimethyl-phenethyl)-2,2,4-trimethyl-1,3-dioxolan as a colorless strongly viscous oil. $[\alpha]_D^{22} = +4.5°$ (c=2.2 in chloroform).

The 2,5-dimethoxy-3,4,6-trimethylbenzyl-triphenylphosphonium chloride used as the starting material was manufactured as follows:

25.7 g of 2,5-dimethoxy-3,4,6-trimethylbenzyl chloride in 100 ml of toluene were heated at reflux with 30 g of triphenylphosphine for 16 hours while stirring. A white suspension formed. The precipitate was filtered off, washed three times with 50 ml of toluene each time and dried up to constant weight in a high vacuum. There were obtained 53.1 g of the desired product as a white powder with a melting point of 230°–231° C.

EXAMPLE 6

Manufacture of (S)-(+)-2,3,6-trimethyl-5-(2,2,4-trimethyl-1,3-dioxolan-4-ethyl)-p-benzoquinone and of (S)-(+)-5-(3,4-dihydroxy-3-methyl-1-butyl)-2,3,6-trimethyl-p-benzoquinone While stirring for 2 minutes at room temperature, 2.01 g of cerium ammonium nitrate in 7.5 ml of water were added dropwise to a solution of 550 mg of (S)-4-(3,5-dimethoxy-3,4,6-trimethyl-phenylethyl)-2,2,4-trimethyl-1,3-dioxolan in 7.5 ml of acetonitrile. After 2 minutes of additional stirring, the reaction mixture was extracted three times with 20 ml of chloroform each time. The combined organic extracts were dried over sodium sulfate, whereafter the solvent was removed. After chromatography of the obtained residue on silica gel with benzene/ethyl acetate (2:1 parts by volume) and ethyl acetate, there were obtained 266 mg of (S)-(+)-2,3,6-trimethyl-5-(2,2,4-trimethyl-1,3-dioxolan-4-ethyl)-p-benzoquinone and 177 mg of (S)-(+)-5-(3,4-dihydroxy-3-methyl-1-butyl)-2,3,6-trimethyl-p-benzoquinone in the form of yellow needles with a melting point of 111°–112°.

EXAMPLE 7

Manufacture of (3S,9aR)-(−)-2,3,4,5,7,9a-hexahydro-3,6,8,9-tetramethyl-3,9a-1-benzoxepin-7-one A mixture of the quinones obtained in accordance with Example 6 was left to stand at room temperature for 16 hours in a mixture of 12.7 ml of methanol and 3.8 ml of 1-N aqueous hydrochloric acid. Thereupon, the acid was neutralized by addition of solid sodium bicarbonate. The reaction mixture was poured into 50 ml of saturated brine and the product was extracted three times with 50 ml of ether. The combined ether extracts were dried over sodium sulfate and then evaporated. By chromatography of the residue on 40 g of silica gel with toluene/ethyl acetate (9:1 and 2:1 parts by volume) as the elution agent there resulted 315 mg of (3S,9aR)-(−)-2,3,4,5,7,9a-hexahydro-3,6,8,9-tetramethyl-3,9a-1-benzoxepin-7-one. After recrystallization from hexane, the product had a melting point of 99°–100°.

In an analogous manner, from the individual quinones manufactured in accordance with Example 6 there could likewise be manufactured (3S,9aR)-(−)-2,3,4,5,7,9a-hexahydro-3,6,8,9-tetramethyl-3,9a-1-benzoxepin-7-one.

EXAMPLE 8

Manufacture of (S)-(+)-6-hydroxy-2,5,7,8-tetramethyl-chroman-2-methanol 250 mg of (3S,9aR)-(−)-2,3,4,5,7,9a-hexahydro-3,6,8,9-tetramethyl-3,9a-1-benzoxepin-7-one in 50 ml of ethanol were hydrogenated with hydrogen gas during 10 minutes in the presence of 200 mg of 5% by weight palladium/carbon. Thereupon, the catalyst was filtered off, the solvent was evaporated off and the residue was chromatographed on silica gel with benzene/ethyl acetate (2:1 parts by volume). There was obtained pure (S)-(+)-6-hydroxy-2,5,7,8-tetramethyl-chroman-2-methanol as colorless crystals with a melting point of 127°–128°.

EXAMPLE 9

Manufacture of (3S,9aR)-(−)-2,3,4,5,7,9a-hexahydro-3,6,8,9-tetramethyl-3,9a-1-benzoxepin-7-one 160 mg of (S)-4-(2,5-dimethoxy-3,4,6-trimethylphenethyl)-2,2,4-trimethyl-1,3-dioxolan in 20 ml of methanol and 4 ml of 0.8-N sulfuric acid were stirred at room temperature overnight with a suspension of 400 mg of cerium sulfate. Thereupon, sodium bicarbonate was added thereto and the reaction mixture was extracted with methylene chloride. After drying of the combined extracts over magnesium sulfate and removal of the solvent, there were obtained 134 mg of a viscous yellow oil. By chromatography of this oil on silica gel with benzene/ethyl acetate (2:1 parts by volume), there were obtained 17 mg of (3S,9aR)-(−)-2,3,4,5,7,9a-hexahydro-3,6,8,9-tetramethyl-3,9a-1-benzoxepin-7-one, which had a melting point of 99°–100° after recrystallization from hexane.

EXAMPLE 10

Manufacture of (S)-2,2,4-trimethyl-1,3-dioxolan-4-acetaldehyde 4.33 g of (S)-2,2,4-trimethyl-1,3-dioxolan-4-ethanol dissolved in 7 ml of absolute methylene chloride were added dropwise to a suspension of 7.59 g of pyridine chlorochromate in 30 ml of absolute methylene chloride. The reaction mixture was stirred at room temperature for 3 hours. By addition of 75 ml of ether, the chromium salt was precipitated and separated by filtration over 120 g of Kieselgel. After removal of the solvent on a rotary evaporator and distillation of the residue at 90°–100°/10 mmHg, there were obtained 3.00 g of (S)-2,2,4-trimethyl-1,3-dioxolan-4-acetaldehyde. $[\alpha]_D^{20} = -35.5°$ (c=1.50; n-hexane).

EXAMPLE 11

Manufacture of α-(2,5-dimethoxy-3,4,6-trimethylphenyl)-2,2,4-(S)-trimethyl-1,3-dioxolan-4-ethanol To 0.8 g of magnesium shavings activated with methyl iodide was added dropwise a solution of 7.77 g of 1-bromo-2,5-dimethoxy-3,4,6-trimethylbenzene in 20 ml of absolute tetrahydrofuran at a rate such that the solvent was brought just to boiling. Subsequently, the reaction mixture was boiled under reflux for an additional hour. To this Grignard solution, cooled down to 0°, were added dropwise 5.0 g of (S)-2,2,4-trimethyl-1,3-dioxolan-4-acetaldehyde. Subsequently, the reaction mixture was stirred at room temperature for a further 4 hours and under reflux for 15 minutes. For the working-up, the reaction mixture was cooled down to 0°, it was treated with 10 ml of saturated ammonium chloride solution followed by 10 ml of 2-N sulfuric acid and extracted with a total of 0.5 l of ether. The organic phase was washed neutral with water and dried over magnesium sulfate. After removal of the solvent on a rotary evaporator and drying of the residue in a high vacuum, there were obtained 10.5 g of a highly viscous oil, which, for purification, was chromatographed on 450 g of Kieselgel with ether/hexane/acetic ester (4:4:1 parts by volume). The yield of α-(2,5-dimethoxy-3,4,6-trimethylphenyl)-2,2,4-(S)-trimethyl-1,3-dioxolan-4-ethanol amounted to 8.83 g; $[\alpha]_D^{20} = -5.5°$ (c=1.20; CHCl$_3$).

EXAMPLE 12

Manufacture of 2,3,6-trimethyl-5-(2,2,4-(S)-trimethyl-1,3-dioxolan-4-β-hydroxyethyl)-p-benzoquinone A solution of 3.38 g of α-(2,5-dimethoxy-3,4,6-trimethyl-phenyl)-2,2,4-(S)-trimethyl-1,3-dioxolan-4-ethanol in 40 ml of acetonitrile was poured into a solution of 11.2 g of Ce(NH$_4$)$_2$(NO$_3$)$_6$ in 40 ml of water and stirred at room temperature for 3.5 minutes. Subsequently, the yellow solution was extracted with a total of 0.5 l of methylene chloride. The combined organic phases were washed neutral firstly with saturated sodium bicarbonate solution, then with saturated common salt solution and dried over magnesium sulfate. After removal of the solvent on the rotary evaporator at 50°, there were obtained 3.30 g of 2,3,6-trimethyl-5-(2,2,4-(S)-trimethyl-1,3-dioxolan-4-β-hydroxyethyl)-p-benzoquinone, which was uniform in a thin-layer chromatogram. The product could be separated by chromatography on Kieselgel with toluene/pentane/acetic acid methyl ether (20:3:3 parts by volume) into the two epimers, which showed the following rotation values: $[\alpha]_D^{20} = -60.2°$ (c=1.6; CHCl$_3$) and $[\alpha]_D^{20} = +17.3°$ (c=2.0; CHCl$_3$).

EXAMPLE 13

Manufacture of (3S,9aR)-(−)-2,3,4,5,7,9a-hexahydro-5-hydroxy-3,6,8,9-tetramethyl-3,9a-epoxy-1-benzoxepin-7-one A mixture of 2.33 g of 2,3,6-trimethyl-5-(2,2,4-(S)-trimethyl-1,3-dioxolan-4-β-hydroxyethyl)-p-benzoquinone, 80 ml of dioxan and 16 ml of 2-N sulfuric acid was stirred at 70° for 2 hours. The cooled solution was neutralized by addition of solid sodium hydrogen carbonate and was subsequently extracted with methylene chloride. The combined organic phases were washed firstly with a saturated common salt solution, then dried with magnesium sulfate. After removal of the solvent on a rotary evaporator at 50°, there were obtained 2.16 g of the (3S,9aR)-(−)-2,3,4,5,7,9a-hexahydro-5-hydroxy-3,6,8,9-tetramethyl-3,9a-epoxy-1-benzoxepin-7-one which was uniform in the thin-layer chromatogram.

For the determination of the optical rotation, a portion of the product was chromatographed on Kieselgel with toluene/acetic ester (1/1 parts by volume): $[\alpha]_D^{20} = +178°$ (c=3.8 CHCL$_3$).

EXAMPLE 14

Manufacture of (S)-(+)-6-hydroxy-2,5,7,8-tetramethylchroman-2-methanol

A mixture of 0.59 g of (3S,9aR)-(−)-2,3,4,5,7,9a-hexahydro-5-hydroxy-3,6,8,9-tetramethyl-3,9a-epoxy-1-benzoxepin-7-one, 0.7 g of palladium-on-barium sulfate (5% by weight) and 3 drops of concentrated perchloric acid in 20 ml of methanol was hydrogenated with ca 120 ml of hydrogen under normal pressure. Subsequently, 2 ml of 2-N sulfuric acid were added and air was conducted into the mixture for 15 hours. The reaction mixture was again hydrogenated with ca 25 ml of hydrogen. After removal of the catalyst by filtration over Hyflo, the filtrate was treated with dilute sodium bicarbonate solution and extracted with ether. The combined organic phases were dried over magnesium sulfate. After distillation of the solvent on a rotary evaporator, there were obtained 0.62 g of brown crystals, which, for purification, was chromatographed on Kieselgel with acetic ester/toluene (1/1 parts by volume). The resulting (S)-(+)-6-hydroxy-hydroxy-2,5,7,8-tetramethylchroman-2-methanol crystallized from methylene chloride/hexane at a yield of 487 mg; melting point 126.5°–128.5°.

EXAMPLE 15

Manufacture of (S)-(+)-6-hydroxy-2,5,7,8-tetramethylchroman-2-methanol 108 mg of (3S,9aR)-(−)-2,3,4,5,7,9a-hexahydro-5-hydroxy-3,6,8,9-tetramethyl-3,9a-epoxy-1-benzoxepin-7-one were hydrogenated at normal pressure together with 100 mg of palladium on carbon (5% by weight) and 20 mg of p-toluenesulfonic acid in 20 ml of methanol. The uptake of hydrogen amounted to 22 ml and the reaction duration amounted to 1 hour. After filtration of the catalyst and removal of the solvent on a rotary evaporator, the residue was chromatographed on a precoated PLC (preparative layer chromatography) Kieselgel plate (Merck) with toluene/acetic ester (1/1 parts by volume), whereby the oxidation to the (S)-(+)-5-(3,4-dihydroxy-3-methyl-1-butyl)-2,3,6-trimethyl-p-benzoquinone took place. There were obtained 70 mg of this product with a melting point of 112°–113°.

The further conversion of this compound into the (3S,9aR)-(−)-2,3,4,5,7,9a-hexahydro-3,6,8,9-tetramethyl-3,9a-1-benzoxepin-7-one as well as its conversion into the (S)-(+)-6-hydroxy-2,5,7,8-tetramethylchroman-2-methanol was effected in a manner analogous to that of Examples 7 or 8.

We claim:
1. A compound of the formula:

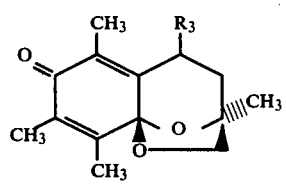

IVA wherein R$_3$ is hydroxy.

* * * * *